United States Patent [19]

Klier et al.

[11] Patent Number: 5,718,888

[45] Date of Patent: Feb. 17, 1998

[54] DEODORANT ACTIVE-SUBSTANCE COMBINATIONS MADE FROM WOOL-GREASE ACIDS AND PARTIAL GLYCERIDES

[75] Inventors: Manfred Klier, Aumühle; Günther Schneider, Hamburg; Bernd Traupe, Hamburg; Ilona Voss, Hamburg; Florian Wolf, Hamburg; Werner Siemanowski, Rheinberg; Karl-Heinz Uhlig, Krefeld; Manfred Röckl, Wedel/Host, all of Germany

[73] Assignee: Beiersdorf AG, Hamburg, Germany

[21] Appl. No.: 530,109

[22] PCT Filed: Mar. 3, 1994

[86] PCT No.: PCT/EP94/00623

§ 371 Date: Dec. 18, 1995

§ 102(e) Date: Dec. 18, 1995

[87] PCT Pub. No.: WO94/21220

PCT Pub. Date: Sep. 29, 1994

[30] Foreign Application Priority Data

Mar. 23, 1993 [DE] Germany .................. 43 09 372.8

[51] Int. Cl.⁶ .................. A61K 7/32; A61K 31/19

[52] U.S. Cl. .................. 424/65; 424/400; 424/401; 514/553

[58] Field of Search .................. 424/65, 400, 401; 514/553

[56] References Cited

U.S. PATENT DOCUMENTS 4,406,884  9/1983  Fawzi et al. .................. 424/81

FOREIGN PATENT DOCUMENTS

| 0 433 132 A1 | 6/1991 | European Pat. Off. |
| 30 09 546 A1 | 9/1981 | Germany |
| 38 18 293 A1 | 12/1989 | Germany |

OTHER PUBLICATIONS

Janistyn, Hugo: Handbuch Der Kosmeticka Und Riechstoffe, 111.Bd., Die Korperpflegemittel, Dr. Alfred Huthig. Verlag Heidelberg, S.683 u. kS.693.

Primary Examiner—Shelley A. Dodson
Attorney, Agent, or Firm—Sprung Kramer Schaefer & Briscoe

[57] ABSTRACT

Cosmetic deodorants containing mixtures of
I) wool wax acids or wool wax acid components, and
II) fatty acid partial glycerides of unbranched fatty acids.

12 Claims, No Drawings

DEODORANT ACTIVE-SUBSTANCE COMBINATIONS MADE FROM WOOL-GREASE ACIDS AND PARTIAL GLYCERIDES

Deodorizing active substance combinations based on wool wax acids and partial glycerides The present invention relates to cosmetic active substance combinations, in particular active substance combinations as the active principle in cosmetic deodorants.

Cosmetic deodorants are intended to remove body odour which is formed when fresh sweat, which is odourless as such, is decomposed by microorganisms. The commercially available cosmetic deodorants are based on different active principles.

In so-called antiperspirants, the production of sweat can be reduced by means of astringents, preferably aluminium salts, such as aluminium chloride hydroxide (aluchlorohydrate). However, the substances used for this purpose not only denature the skin proteins but also engage drastically in the heat metabolism of the underarm region, depending on their dosage rate, and should only be used in exceptional cases.

It is possible to reduce the bacterial flora on the skin by using antimicrobial substances in cosmetic deodorants. In the ideal case, only those microorganisms should be reduced in an effective manner which cause odour. However, it has emerged in practice that the entire microbial flora of the skin can be adversely affected.

Perspiration itself is not affected by this; in the ideal case, only microbial decomposition of the sweat is stopped temporarily.

It is also conventional to use a combination of astringents together with antimicrobial active substances in one and the same composition. However, the disadvantages of both classes of active substances cannot be overcome entirely in this manner.

Finally, it is also possible to mask body odour by odoriferous substances, a method which meets the aesthetic expectations of the consumer the least since the mixture of body odour and perfume smells rather unpleasant.

Even so, most of the cosmetic deodorants, like most cosmetics in general, are perfumed even when they contain deodorizing active substances. Perfuming a cosmetic product can also be used for improving its attraction to the consumer or for styling a product in a certain manner.

Perfuming cosmetic preparations which contain active substances, in particular cosmetic deodorants, however, is frequently not without problems since active substances and perfume components can occasionally react with each other and neutralize each other's activities.

Deodorants should meet the following conditions:

1) They should deodorize in a reliable fashion.
2) The natural biological processes must not be adversely affected by the deodorants.
3) The deodorants must be non-hazardous when they are overdosed or otherwise not used as intended.
4) They should not accumulate on the skin after repeated use.
5) They should be capable of being readily incorporated into conventional cosmetic formulations.

Deodorants which are known and conventionally used are both liquid deodorants, for example aerosols or roll-on preparations and the like, and solid preparations, for example deodorant sticks, powders, powder sprays, compositions for female hygiene, etc.

It was therefore the object of the present invention to develop cosmetic deodorants which do not have the disadvantages of the prior art. In particular, it was intended that the deodorants should not, to a large extent, harm the microbial flora on the skin but should selectively reduce the number of those micro-organisms which are responsible for body odour.

Another object of the invention was to develop cosmetic deodorants which are distinguished by good tolerance by the skin. It was intended that the deodorizing active principles should on no account accumulate on the skin.

A further object was to develop cosmetic deodorants which are compatible with the largest possible number of conventional cosmetic auxiliaries and additives, in particular with the perfume components which are important especially in those formulations which have a deodorizing or antiperspiratory activity.

A further object of the invention was to provide cosmetic deodorants which are effective over a longer period, namely in the order of magnitude of at least half a day, without their activity noticeably declining.

Finally, it was an object of the present invention to develop deodorizing cosmetic principles which can be incorporated as widely as possible into a wide range of product forms of cosmetic deodorants and without being restricted to one or a few specific product forms.

Surprisingly, it has been found, and this is how all these objects were achieved, that cosmetic deodorants containing mixtures of I) wool wax acids or wool wax acid components, and II) fatty acid partial glycerides of unbranched fatty acids overcome the disadvantages of the prior art.

The term wool wax or wool grease is used to designate the greasy to waxy constituent of the raw sheep's wool which is obtained when raw wool is washed. The wool wax is composed of a mixture of fatty acid esters of higher alcohols and free fatty acids.

The main constituents of the wool wax acids are (a) saturated unsubstituted carboxylic acids of the formula

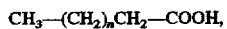

(b) α-hydroxycarboxylic acids of the formula

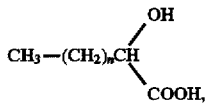

(c) Ω-hydroxycarboxylic acids of the formula

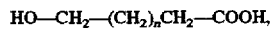

(d) isocarboxylic acids of the formula

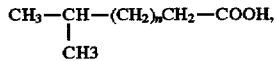

(e) α-hydroxy-isocarboxylic acids of the formula

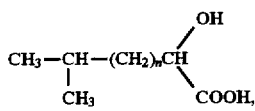

(f) Ω-hydroxy-isocarboxylic acids of the formula

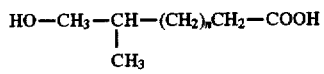

(g) ante-isocarboxylic acids of the formula

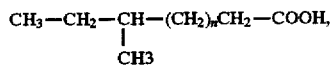

(h) α-hydroxy-ante-isocarboxylic acids of the formula

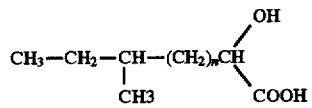

(i) Ω-hydroxy-ante-isocarboxylic acids of the formula

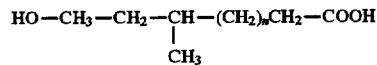

n usually assumes values from 7–31.

Representative compositions of the wool wax acids are described, for example, in "Parfümerie und Kosmetik" [Perfumery and Cosmetics], Year 59, No. 12/78, pp. 429, 430, and in "Lexikon der Hilfsstoffe für Pharmazie, Kosmetik und angrenzende Gebiete" [Encyclopaedia of auxiliaries for pharmacology, cosmetology and related fields] by H. P. Fiedler, 1989, 3rd Edition, Editio Cantor Aulendorf.

Crude wool wax acids are not suitable for cosmetic purposes, distilled wool wax acids usually being employed instead. This fact and suitable processes for refining crude wool wax acids are known to a person skilled in the art.

Wool wax acids are characteristically composed of approximately 60% saturated, unsubstituted carboxylic acids, approximately 30% α-hydroxycarboxylic acids and approximately 5% Ω-hydroxycarboxylic acids, the remainder of approximately 5% essentially being formed of the other, abovementioned types of carboxylic acids.

The wool wax acids according to the invention are, in particular, advantageously distinguished by the following characterizing parameters:
Melting point: 50°–54° C.
Acid value: 166–170
Saponification value: 175–190
OH value: 60–80
Iodine value: 7–12

Even though it is known from the paper "Antimicrobial Factors in Wool Wax" (Australian Journal of Chemistry, 1971, 24, pages 153 et seq.) that some batches of wool wax contain antimicrobial factors, no mention is made in the reference cited which foreshadows the present invention.

It is assumed that the α-hydroxycarboxylic acids in particular contribute substantially to the action according to the invention. Cosmetic deodorants containing mixtures of I) α-hydroxycarboxylic acids of the formula

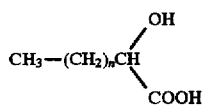

and/or
α-hydroxy-isocarboxylic acids of the formula

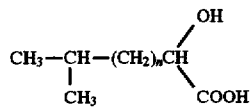

and/or
α-hydroxy-ante-isocarboxylic acids of the formula

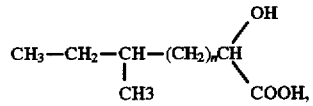

where n is in each case a number from 7 to 31, and
II) fatty acid partial glycerides of unbranched fatty acids are therefore also according to the invention.

It is particularly advantageous within the scope of the present invention to use α-hydroxycarboxylic acids which represent $C_{16}$ bodies, i.e. which have a branched or unbranched $C_{14}H_{29}$ chain on the α-carbon atoms.

It is furthermore advantageous to use mixtures of wool wax acids in which the α-hydroxycarboxylic acid content is 20–30% by weight based on the total composition.

Partial glycerides within the scope of the present invention are:

(1) Monocarboxylic acid monoesters and monocarboxylic acid diesters of glycerol. These are favourably characterized by a structure as follows:

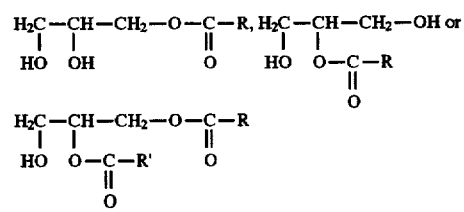

where R and R' independently of one another represent an unbranched alkyl radical having 5 to 17 C atoms.

(2) Monocarboxylic acid monoesters of diglycerol.
(3) Monocarboxylic acid monoesters of triglycerol.

According to the invention, the di- or triglycerol units of the partial glycerides according to the invention are in the form of linear, unbranched molecules, i.e. "monoglycerol molecules" which are etherified via the respective OH groups in the 1- or 3-position.

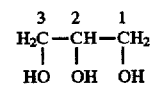

(glycerol="monoglycerol")

A small amount of cyclic di- or triglycerol units and glycerol molecules which are etherified via the OH groups in the 2-position can be accepted. It is advantageous, however, to keep the quantity of such impurities as small as possible.

The diglycerol-based partial glycerides according to the invention are preferably monocarboxylic acid monoesters and are preferably characterized by the following structure:

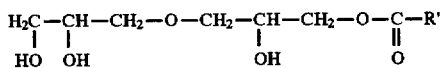

where R' represents an unbranched alkyl radical having 5 to 17 C atoms.

The triglycerol-based partial glycerides according to the invention are preferably monocarboxylic acid monoesters and are preferably characterized by the following structure:

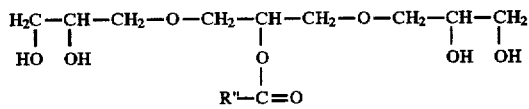

where R" represents an Unbranched alkyl radical having 5 to 17 C atoms.

The fatty acids or monocarboxylic acids on which these esters are based are

| hexanoic acid | (caproic acid) | (R' or R" = —C$_5$H$_{11}$), |
|---|---|---|
| heptanoic acid | (oenanthic acid) | (R' or R" = —C$_6$H$_{13}$), |
| octanoic acid | (caprylic acid) | (R' or R" = —C$_7$H$_{15}$), |
| nonanoic acid | (perlargonic acid) | (R' or R" = —C$_8$H$_{17}$), |
| decanoic acid | (capric acid) | (R' or R" = —C$_9$H$_{19}$), |
| undecanoic acid | | (R' or R" = —C$_{10}$H$_{21}$), |
| 10-undecenoic acid | | (R' or R" = —C$_{10}$H$_{19}$), |
| dodecanoic acid | (lauric acid) | (R' or R" = —C$_{11}$H$_{23}$), |
| tridecanoic acid | | (R' or R" = —C$_{12}$H$_{25}$), |
| tetradecanoic acid | (myristic acid) | (R' or R" = —C$_{13}$H$_{27}$), |
| pentadecanoic acid | | (R' or R" = —C$_{14}$H$_{29}$), |
| hexadecanoic acid | (palmitic acid) | (R' or R" = —C$_{15}$H$_{31}$), |
| heptadecanoic acid | (margaric acid) | (R' or R" = —C$_{16}$H$_{33}$), |
| octadecanoic acid | (stearic acid) | (R' or R" = —C$_{17}$H$_{35}$). |

It is particularly favourable to select R' and R" from amongst the group comprising the unbranched alkyl radicals having uneven C numbers, in particular 9, 11 and 13 C atoms.

In general, the diglycerol esters are preferred, according to the invention, to the triglycerol esters.

Very particularly favourable are

| diglyceryl monocaprate | (DMC) | R' = 9 |
|---|---|---|
| triglyceryl monolaurate | (TML) | R" = 11 |
| diglyceryl monolaurate | (DML) | R' = 11 |
| triglyceryl monomyristate | (TMM) | R" = 13. |

Diglyceryl monocaprate (DMC) has emerged as preferred partial glyceride according to the invention.

Particularly advantageous are partial glycerides based on those monocarboxylic acid esters which can be obtained by a process as described in DE-A 38 18 293.

In an advantageous embodiment of the present invention, mixtures of one or more diglycerol monocarboxylic acid esters with one or more triglycerol monocarboxylic acid esters are used as partial glycerides of unbranched fatty acids.

In a further advantageous embodiment of the present invention, one or more diglycerol monocarboxylic acid esters and/or one or more triglycerol monocarboxylic acid esters in combination with other active substances (substitute active substances), auxiliaries, extenders and/or additives conventionally used in cosmetics are used as partial glycerides of unbranched fatty acids.

The extenders and/or replacement active substances are then advantageously present in a concentration of up to 50 parts by weight, preferably up to 35 parts by weight, based on 100 parts by weight of the total amount, which is composed of the diglycerol and/or triglycerol monocarboxylic acid ester(s) and these replacement active substances and/or extenders.

In a further advantageous embodiment of the present invention, the wool wax acid components employed are one or more (a) saturated unsubstituted carboxylic acids of the formula

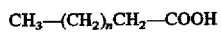

and/or (b) α-hydroxycarboxylic acids of the formula

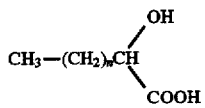

and/or (c) Ω-hydroxycarboxylic acids of the formula

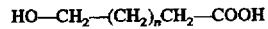

and/or (d) isocarboxylic acids of the formula

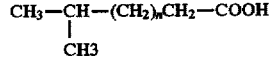

and/or (e) α-hydroxy-isocarboxylic acids of the formula

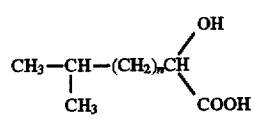

and/or (f) Ω-hydroxy-isocarboxylic acids of the formula

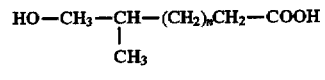

and/or (g) ante-isocarboxylic acids of the formula

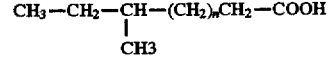

and/or (h) α-hydroxy-ante-isocarboxylic acids of the formula

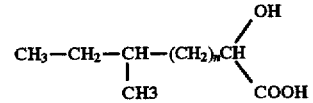

and/or (i) Ω-hydroxy-ante-isocarboxylic acids of the formula

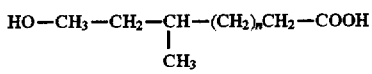

where n assumes values from 7–31, in combination with other active substances (substitute active substances), auxiliaries, extenders and/or additives conventionally used in cosmetics.

The extenders and/or replacement active substances are then advantageously present in a concentration of up to 50 parts by weight, preferably up to 35 parts by weight, based on 100 parts by weight of the total amount which is composed of the total of the wool wax acid components and these replacement active substances and/or extenders.

Cosmetic deodorants which contain

I) wool wax acids or wool wax acid components, and

II) one or more substances selected from amongst the group comprising
diglyceryl monocaprate (DMC),
triglyceryl monolaurate (TML),
diglyceryl monolaurate (DML) and
triglyceryl monomyristate (TMM), are regarded as a particularly advantageous embodiment of the present invention.

Other advantageous embodiments of the present invention are cosmetic deodorants which contain I) α-hydroxycarboxylic acids of the formula

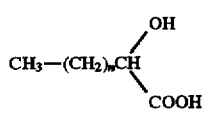

and/or
α-hydroxy-isocarboxylic acids of the formula

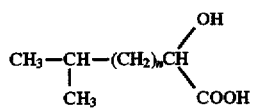

and/or
α-hydroxy-ante-isocarboxylic acids of the formula

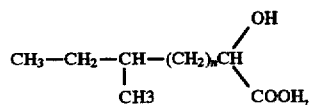

where n in each case denotes a number from 7 to 31, and

II) diglyceryl monocaprate (DMC) and/or
triglyceryl monolaurate (TML) and/or
diglyceryl monolaurate (DML) and/or
triglyceryl monomyristate (TMM).

It is advantageous to select the content of

I) wool wax acids or wool wax acid components, and

II) fatty acid partial glycerides of unbranched fatty acids in such a manner that the ratios of I) to II) are 5:1 to 1:5, in particular approximately 1:1, very particularly advantageously approximately 1:3.

A method for controlling human body odour caused by microbial decomposition of apocrine sweat is also in accordance with the invention, characterized in that an effective amount of mixtures of I) wool wax acids or wool wax acid components, and II) fatty acid partial glycerides of unbranched fatty acids, in particular mixtures of I) α-hydroxycarboxylic acids of the formula

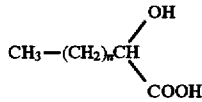

and/or
α-hydroxy-isocarboxylic acids of the formula

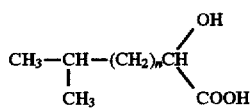

and/or
α-hydroxy-ante-isocarboxylic acids of the formula

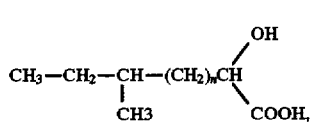

where n in each case denotes a number from 7 to 31, and

II) fatty acid partial glycerides of unbranched fatty acids, which can optionally be present in a suitable cosmetic carrier, is applied to the skin.

Finally, the use of mixtures of

I) wool wax acids or wool wax acid components, and

II) fatty acid partial glycerides of unbranched fatty acids, in particular mixtures of I) α-hydroxycarboxylic acids of the formula

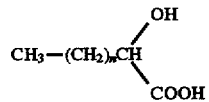

and/or
α-hydroxy-isocarboxylic acids of the formula

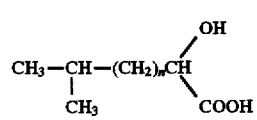

and/or
α-hydroxy-ante-isocarboxylic acids of the formula

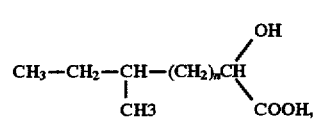

where n in each case denotes a number from 7 to 31, and

II) fatty acid partial glycerides of unbranched fatty acids, which can optionally be present in a suitable cosmetic carrier, for controlling Gram-positive, in particular coryneform, bacteria, or the use of mixtures of I) wool wax acids or wool wax acid components, and II) fatty acid partial glycerides of unbranched fatty acids, in particular mixtures of I) α-hydroxycarboxylic acids of the formula

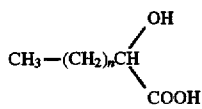

and/or

α-hydroxy-isocarboxylic acids of the formula

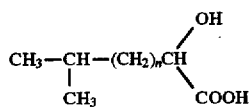

and/or

α-hydroxy-ante-isocarboxylic acids of the formula

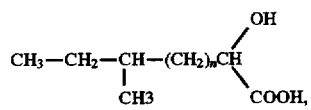

where n in each case denotes a number from 7 to 31, and

II) fatty acid partial glycerides of unbranched fatty acids, which can optionally be present in a suitable cosmetic carrier, for preventing the growth of Gram-positive, in particular coryneform, bacteria, is also in accordance with the invention.

The cosmetic deodorants according to the invention are particularly advantageously characterized in that the wool wax acids or the wool wax acid components are present at concentrations of 0.05–10.00% by weight, preferably 0.1–5.0% by weight, in each case based on the total weight of the preparations.

The cosmetic deodorants according to the invention are also particularly advantageously characterized in that the fatty acid partial glycerides of unbranched fatty acids are present at concentrations of 0.05–10.00% by weight, preferably 0.1–5.0% by weight, in each case based on the total weight of the preparations.

The cosmetic deodorants according to the invention can be in the form of aerosols, i.e. preparations which can be sprayed from aerosol containers, squeeze bottles or by means of a pumping device, or in the form of liquid compositions which can be applied by means of roll-on devices, as deodorant sticks and in the form of W/O or O/W emulsions, for example creams or lotions, which can be applied from normal bottles and containers. Furthermore, the cosmetic deodorants can advantageously be in the form of deodorizing tinctures, deodorizing compositions for female hygiene, deodorizing shampoos, deodorizing shower or bath preparations, deodorizing powders or deodorizing powder sprays.

Conventional cosmetic carriers which can be used for making the deodorizing preparations according to the invention are, besides water, ethanol and isopropanol, glycerol and propylene glycol, fatty or fat-like skincare substances, such as decyl oleate, cetyl alcohol, cetylstearyl alcohol and 2-octyldodecanol, in the ratios conventionally used for such preparations, and mucilage-forming substances and thickeners, for example hydroxyethyl- or hydroxypropylcellulose, polyacrylic acid, polyvinylpyrrolidone, and also small amounts of cyclic silicone oils (polydimethylsiloxanes) and liquid, low-viscosity polymethylphenylsiloxanes.

Suitable propellants for cosmetic deodorants according to the invention which can be sprayed from aerosol containers are the customary, known, volatile, liquefied propellants, for example hydrocarbons (propane, butane, isobutane), which can be used by themselves or in the form of mixtures with one another. Compressed air can also be used advantageously.

Of course, it is known to the person skilled in the art that there are propellants which are non-toxic per se and which would, in principle, be suitable for the present invention, but which should nevertheless not be used since their effect on the environment is unacceptable or because of other related circumstances, in particular fluorochlorohydrocarbons (FCHC).

Emulsifiers for the preparation of the cosmetic deodorants according to the invention which should advantageously be applied to the desired areas of the skin in the form of liquid preparations by means of a roll-on device and which can be used in the preparations in small amounts, for example 2 to 5% by weight based on the total composition, and which have proved suitable are non-ionic types, such as polyoxyethylene fatty alcohol ethers, such as cetostearyl alcohol polyethylene glycol ether having 12 or 20 ethylene oxide units added on to each molecule, cetostearyl alcohol and sorbitan esters and sorbitan ester/ethylene oxide compounds (for example sorbitan monostearate and polyoxyethylene sorbitan monostearate) and long-chain, higher-molecular-weight waxy polyglycol ethers.

In addition to those mentioned above, constituents which can be admixed to the deodorizing cosmetic preparations according to the invention, whose pH is preferably adjusted to 4.0 to 9.0, in particular 5.0 to 6.5, using customary buffer mixtures, are perfume, colorants, antioxidants (for example α-tocopherol and its derivatives or butylhydroxytoluene (BHT=2,6-di-tert-butyl-4-methylphenol) in amounts of 0.01 to 0.03% based on the total composition), suspending agents, buffer mixtures or other conventionally used cosmetic basic materials.

The pH of the cosmetic deodorants according to the invention is preferably adjusted in such a manner that the acid components according to the invention are essentially present in the form of acids, not of anions, i.e. preferably in the acidic to neutral range, in particular in a pH range of 5.0 to 6.5.

The amounts of cosmetic carriers and perfume to be employed in each case can be determined readily by a person skilled in the art by simple experimentation, depending on the nature of the product involved.

If appropriate, substances and perfume oils which are also suitable for perfuming are those which are stable, do not irritate the skin and have already as such antibacterial or bacteriostatic properties.

Apart from specific preparations which are shown separately in the examples, the cosmetic preparations are prepared in the customary manner, mostly by simple mixing with stirring, if appropriate with gentle heating. There are no problems. For emulsions, for example, the fatty phase and the aqueous phase are prepared separately, if appropriate with heating, and then emulsified.

Apart from this, the conventional rules for composing cosmetic formulations, with which the person skilled in the art will be familiar, are to be followed.

If the compositions according to the invention are to be incorporated into powder sprays, the suspension bases for these sprays can be selected advantageously from amongst the group comprising silica gels (for example those which are commercially available under the trade name Aerosil®), kieselguhr, talc, modified starch, titanium dioxide, silk powder, nylon powder, polyethylene powder and related substances.

What follows are advantageous use examples of the present invention. Unless specifically indicated otherwise, the figures given are always % by weight. In the examples, the term "WWA" is a wool wax acid fraction obtained from crude wool wax acid by flash distillation at $10^{-1}$ bar and a distillation temperature interval of 150°–200° C. α-Hydroxycarboxylic acids account for approximately 22–27% of this.

EXAMPLE 1

| Gel roll-on I-III | | | |
|---|---|---|---|
| | I | II | III |
| PEG-40 hydrogenated castor oil | 1.75 | 1.50 | 1.75 |
| WWA | 0.40 | 0.40 | 0.40 |
| Diglyceryl monocaprate | 0.75 | 0.60 | — |
| Diglyceryl monolaurate | — | — | 0.90 |
| Triglyceryl monolaurate | — | 0.90 | 0.90 |
| Ethanol | 62.00 | 62.00 | 60.00 |
| Perfume | q.s. | q.s. | q.s. |
| Fully demineralized water | - in each case to 100.00 - | | |

EXAMPLE 2

| Emulsion roll-on I-III | | | |
|---|---|---|---|
| | I | II | III |
| PEG-21 stearyl ether (Brij 721) | 1.50 | 1.60 | 1.50 |
| PEG-2 stearyl ether (Brij 72) | 2.50 | 2.80 | 2.50 |
| Mineral oil DAB 9 | 4.00 | 4.50 | 4.00 |
| Isopropyl palmitate | 3.50 | 3.50 | 4.00 |
| Methyl/propylparaben | 0.15 | 0.15 | 0.15 |
| WWA | 0.70 | 0.70 | 0.70 |
| Diglyceryl caprate | 0.70 | — | 0.50 |
| Diglyceryl laurate | — | 0.90 | — |
| Triglyceryl myristate | — | — | 0.70 |
| Perfume | q.s. | q.s. | q.s. |
| Fully demineralized water | - in each case to 100.00 - | | |

EXAMPLE 3

| Pump diffuser I-II | | |
|---|---|---|
| | I | II |
| Ethanol | 68.00 | 60.00 |
| 1,2-Propylene glycol | 1.80 | 1.80 |
| WWA | 0.30 | 0.30 |
| Diglyceryl monocaprate | 0.70 | — |
| Diglyceryl monolaurate | — | 1.1 |
| Perfume | q.s. | q.s. |
| Fully demineralized water | in each case to 100.00 | |

EXAMPLE 4

| Gel stick I-II | | |
|---|---|---|
| | I | III |
| Stearic acid | 6.00 | 6.00 |
| Ceteareth-15 | 2.75 | 2.75 |
| WWA | 2.00 | 2.00 |
| Diglyceryl monocaprate | 1.50 | — |
| Triglyceryl monolaurate | — | 1.60 |
| Ethanol | 16.00 | 16.00 |
| NaOH | 1.10 | 1.05 |
| Perfume | q.s. | q.s. |
| Fully demineralized water | - in each case to 100.00 - | |

EXAMPLE 5

| Deodorant cream I-II | | |
|---|---|---|
| | I | II |
| Mineral oil DAB 9 | 3.50 | 3.50 |
| PEG-40 stearate | 4.00 | 4.00 |
| Cetyl alcohol | 3.50 | 3.50 |
| Ethylhexyl stearate | 0.90 | 0.90 |
| Propylene glycol | 1.00 | 1.00 |
| Methyl/propylparaben | 0.15 | 0.15 |
| WWA | 0.30 | 0.30 |
| Diglyceryl monocaprate | 0.60 | — |
| Triglyceryl monolaurate | — | 1.1 |
| Perfume | q.s. | q.s. |
| Fully demineralized water | in each case to 100.00 | |

We claim:

1. Cosmetic deodorants containing mixtures of

I) wool wax acids or wool wax acid components, and

II) fatty acid partial glycerides of unbranched fatty acids.

2. Cosmetic deodorants according to claim 1, wherein the fatty acid partial glycerides are selected from amongst the group of the (1) glycerol monocarboxylic acid monoesters, in each case with the structures

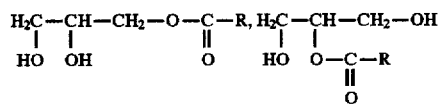

where R represents an unbranched alkyl radical having 5 to 17 C atoms, (2) diglycerol monocarboxylic acid monoesters of the structures

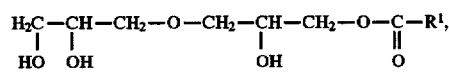

where R' represents an unbranched alkyl radical having 5 to 17 C atoms, (3) triglycerol monocarboxylic acid monoesters having the structures

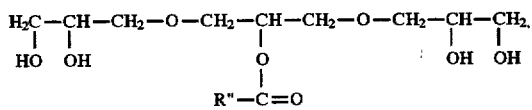

where R" represents an unbranched alkyl radical having 5 to 17 C atoms.

3. Cosmetic deodorants according to claim 1, wherein they contain

II) one or more substances selected from amongst the group comprising
diglyceryl monocaprate (DMC),
triglyceryl monolaurate (TML),
diglyceryl monolaurate (DML) and
triglyceryl monomyristate (TMM).

4. Cosmetic deodorants according to claim 1, wherein the wool wax acid components are selected from amongst the group comprising (a) saturated unsubstituted carboxylic acids of the formula

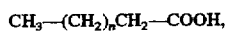

(b) α-hydroxycarboxylic acids of the formula

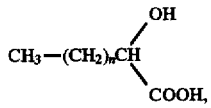

(c) Ω-hydroxycarboxylic acids of the formula

(d) isocarboxylic acids of the formula

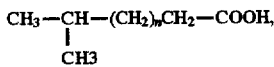

e) α-hydroxy-isocarboxylic acids of the formula

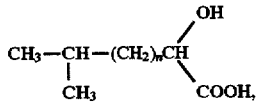

(f) Ω-hydroxy-isocarboxylic acids of the formula

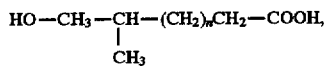

(g) ante-isocarboxylic acids of the formula

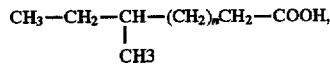

(h) α-hydroxy-ante-isocarboxylic acids of the formula

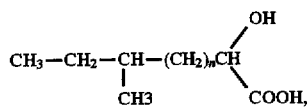

(i) Ω-hydroxy-ante-isocarboxylic acids of the formula

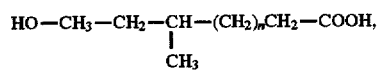

n in each case assuming values from 7–31.

5. Cosmetic deodorants according to claim 1, wherein the wool wax acids or the wool wax acid components are present at concentrations of 0.05–10.00% by weight, in each case based on the total weight of the preparations.

6. Cosmetic deodorants according to claim 1, wherein the fatty acid partial glycerides of unbranched fatty acids are present at concentrations of 0.05–10.00% by weight, in each case based on the total weight of the preparations.

7. Cosmetic deodorants according to claim 1, wherein they are in the form of aerosols, i.e. preparations which can be sprayed from aerosol containers, squeeze bottles or by means of a pumping device, liquid compositions which can be applied by means of roll-on devices, deodorant sticks, W/O or O/W emulsions, for example creams or lotions, which can be applied from normal bottles and containers, deodorizing tinctures, deodorizing compositions for female hygiene, deodorizing shampoos, deodorizing shower or bath preparations, deodorizing powders or deodorizing powder sprays.

8. Cosmetic deodorants according to claim 5, wherein said wool wax acids or wool wax acid components are present at concentrations of 0.1–5.0% by weight.

9. Cosmetic deodorants according to claim 6, wherein said wool wax acids or wool wax acid components are present at concentrations of 0.1–5.0% by weight.

10. Method for controlling Gram-positive bacteria or for preventing their growth comprising applying to the habitat of said bacteria an effective amount of mixtures of I) wool wax acids or wool wax acid components, and II) fatty acids partial glycerides of unbranched fatty acids.

11. Method according to claim 10, wherein said bacteria are coryneform bacteria.

12. Method of controlling human body odour caused by microbial decomposition of apocrine sweat, wherein an effective amount of mixtures of I) wool wax acids or wool wax acid components, and II) fatty acid partial glycerides of unbranched fatty acids, which can optionally be present in a suitable cosmetic carrier, is applied to the skin.

* * * * *